United States Patent [19]

Tellier et al.

[11] 4,178,292

[45] Dec. 11, 1979

[54] PROCESS FOR THE PREPARATION OF OXAZIRIDINE

[75] Inventors: Pierre Tellier, Oullins; Francis Weiss, Benite, both of France

[73] Assignee: Produits Chimiques Ugine Kuhlmann, Paris, France

[21] Appl. No.: 625,113

[22] Filed: Oct. 23, 1975

Related U.S. Application Data

[63] Continuation of Ser. No. 412,407, Nov. 2, 1973, abandoned.

[30] Foreign Application Priority Data

Nov. 3, 1972 [FR] France .................. 72.38897

[51] Int. Cl.² .................. C07D 273/00; C07D 413/04
[52] U.S. Cl. .................. 260/333; 546/275; 546/256
[58] Field of Search .................. 260/333; 546/256, 275

[56] References Cited

U.S. PATENT DOCUMENTS

| | | | |
|---|---|---|---|
| 2,784,182 | 3/1957 | Krimm et al. | 260/239 |
| 2,833,787 | 5/1958 | Carlson et al. | 260/348.5 L |
| 3,156,709 | 11/1964 | Allan | 260/348.5 L |
| 3,177,227 | 4/1965 | Payne | 260/343.6 |
| 3,597,459 | 8/1971 | Mimoun et al. | 260/348.5 V |
| 3,819,653 | 6/1974 | Schirmann et al. | 260/333 |

FOREIGN PATENT DOCUMENTS 45-19894 7/1970 Japan.

OTHER PUBLICATIONS

L. Horner et al., Chem. Berichte, vol. 90, (1957), pp. 2184-2189.
Payne et al., Jour. Org. Chem., vol. 26, Mar. 1961, pp. 659-663.
G. A. Tolstikov et al., Tetrahedron Letters, No. 30, pp. 2807-2808.
A. M. Mattucci et al., Chem. Soc. Jour. D, Chem. Communications, (1970), pp. 1198-1199.
A. Weissberger, Heterocyclic Compounds with Three- and Four-Membered Rings, Part One, (1964), p. 630.
Chem. Abstracts, vol. 66, (1967), p. 94502c; Memoirs of the Faculty of Engineering Nagoya University, vol. 18, No. 1, pp. 1-33, (Sawaki et al.).

*Primary Examiner*—Norma S. Milestone
*Attorney, Agent, or Firm*—Pennie & Edmonds

[57] ABSTRACT

This invention relates to a method for preparing oxaziridines which comprises reacting hydrogen peroxide with an azomethinic derivative or with a mixture of a carbonyl compound and a primary amine in the presence of catalytic amounts of selenium or of oxygenated compounds of selenium.

3 Claims, No Drawings

PROCESS FOR THE PREPARATION OF OXAZIRIDINE

This is a continuation, of application Ser. No. 412,407, filed Nov. 2, 1973, now abandoned.

BACKGROUND OF THE INVENTION

I. Field of the Invention

This invention relates to the preparation of oxaziridines and specifically to the preparation of oxaziridines by the method of reacting hydrogen peroxide with an azomethinic derivative or with a mixture of a carbonyl compound and a primary amine.

II. Description of the Prior Art

It is known that oxaziridines can be prepared by reacting hydrogen peroxide with an azomethine or with a mixture of a carbonyl compound and a primary amine (British Patent No. 743,940 of Jan. 25, 1956.) Nevertheless, the reaction is slow, it is necessary to work at a relatively high temperature, and the yields of oxaziridine are poor. It has in fact been shown (Angew. Chem. 1965-77-548) that in this case an aminoperoxide is first formed and must then be dehydrated by heating to form oxaziridine.

The preparation of oxaziridine by reacting hydrogen peroxide in the presence of a nitrile with an imine has been previously described in commonly assigned pending U.S. application Ser. No. 193,564, filed Oct. 28, 1971 now U.S. Pat. No. 3,819,653.

SUMMARY OF THE INVENTION

It has been discovered that oxaziridines, which are sometimes referred to as oxaziranes or isonitrones, can be prepared rapidly, at moderate temperatures, and in excellent yields according to the process of this invention.

Broadly, the method of this invention involves the preparation of oxaziridines by reacting hydrogen peroxide with an azomethinic derivative or with a mixture of a carbonyl commpound and a primary amine in the presence of catalytic amounts of selenium or of oxygenated compounds of selenium.

DESCRIPTION OF THE PREFERRED EMBODIMENTS

The azomethine compounds, which are sometimes referred to as Schiff bases, are well known in the art and can have the general formula

Azomethine compounds can be prepared by reacting aldehydes or ketones with primary amines.

The following are non-limitative examples of reactants which can be used within the scope of this invention:

aldehydes: acetaldehyde, propionaldehyde, n-butyraldehyde, isobutyraldehyde, n-valeraldehyde, pivalaldehyde, oenanthal, ethyl-2 hexanal, hexahydrobenzaldehyde, benzaldehyde monochlorobenzaldehyde, o-, m-, and p-nitrobenzaldehyde, β-methoxypropionaldehyde, β-ethoxypropionaldehyde, glyoxal, succinic, glutaric, adipic aldehydes;

ketones: acetone, butanone-2, pentanone-2, pentanone-3, methylisopropylketone, methylisobutylketone, methylcylohexylketone, acetophenone, benzophenone, cyclobutanone, cyclopentanone, cyclohexanone, methyl-2 cyclohexanone, methyl-3 cyclohexanone, methyl-4 cyclohexanone, cycloheptanone, cyclooctanone, cyclodecanone, cyclododecanone, cyclohexane diketone-1,4; and primary amines: methylamine, ethylamine, n-propylamine, isopropylamine, n-butylamine, isobutylamine, mine, isopropylamine, n-butylamine, isobutylamine, t-butylamine, amylamines, cyclohexylamine, n-dodecylamine, monoethanolamine, methoxy-2, ethylamine, β-aminopropionitrile, β-aminopropionamide, aniline, toluidines, chloro- and dichloro-anilines, chloro- and dichloro-toluidines, bromoanilines, fluoroanilines, nitro- and dinitro-anilines, nitro and dinitrotoluidines, o-, m-, and p-anisidines, trifluoromethylanilines, anthranilic acid, sulfanilic acid, α-napththylamine, β-naphththylamine, aminopyridines, ethylenediamine, hexamethylenediamine.

The azomethines may be separately synthetized by known methods and reacted in the pure state with hydrogen peroxide. It is, however, also possible to use a mixture of aldehydes or ketones and a primary amine. In this case, although the formation of the azomethines is a balanced reaction, the action of hydrogen peroxide in the presence of selenium compounds is sufficiently rapid for the yield of oxaziridine to be excellent.

The following are non-limitative examples of oxygenated compounds which can be used as catalysts within the scope of the present invention: selenium dioxide, selenious acid, alkali or alkaline earth metal salts of selenious acid, and alkyl esters of selenious acid.

There is no particular limitation of the amount of catalyst to be added. For reasons of economy the concentration of catalyst may vary between 0.001 and 0.2 molecules, and preferably between 0.01 and 0.1 molecules of catalyst per molecule of hydrogen peroxide.

For the purpose of carrying out the process according to the invention the reagents are brought into contact in a liquid medium, and they may be mixed in any order or in any combination. The use of a solvent is generally advantageous in order to at least partially homogenize the reaction medium. The preferred solvents are water and saturated alcohols containing 1 to 6 carbon atoms.

The reaction may be carried out within a wide temperature range advantageously varying from between about $-20°$ C. to $+100°$ C.

The reagents may be used in stoichiometric proportions, but there may be a deficiency or an excess of one or the other of them in relation to these proportions.

The reagents may be used in their usual commercial form, in the pure state, or dissolved in water or a solvent. For example, the lower aliphatic amines and hydrogen peroxide may be used in the form of commercially available aqueous solutions.

It may be advantageous to add to the medium one or more known stabilizers for hydrogen peroxide.

After the reaction, the oxaziridines can be separated from the reactional mixture by methods known per se, such as extraction by means of an immiscible solvent, fractional distillation, or a combination of these two methods.

The oxaziridines of this invention are useful as intermediates, e.g. for the synthesis of lactams such as the N-substituted lactams in a manner well known to those skilled in the art.

In the following examples, which illustrate the present invention without limiting it, the operation was carried out in glas reactors of suitable dimensions and equipped with a mechanical agitation means and a condenser.

EXAMPLE 1

A solution of 61 g (0.4 mole) isobutylidene cyclohexylamine, 1.25 g disodium salt of ethylenediaminetetracetic acid and 1.10 g selenium dioxide in 50 g methanol was placed in a reactor, and then within a period of 1 hour, at 50° C., 25 g (0.5 mole) of a 68% aqueous solution of hydrogen peroxide were added. The reaction was allowed to continue for an additional 15 minutes, whereupon the methanol was eliminated under reduced pressure (200 mm Hg). Extraction was effected first with 50 cc of chloroform and then twice with 25 cc of chloroform. The organic phases were united and dried over sodium sulphate. The chloroform was evaporated under reduced pressure. Distillation of the residue at 42°–44° C. and 0.2 mm Hg produced 61 g (0.36 mole) of cyclohexyl-2 isopropyl-3 oxaziridine which was identified by infrared spectrography. The yield was 90%, compared to the imine used.

EXAMPLE 2

A solution of 34 g (0.3 mole) isobutylidene isopropylamine, 0.94 g disodium salt of ethylenediaminetetracetic acid, and 0.82 g selenium dioxide in 37.5 g methanol was placed in a reactor, and then within a period of one hour, at 50° C., 18.7 g (0.375 mole) of a 68% aqueous solution of hydrogen peroxide were added. The operation was continued as in Example 1. Distillation at 43° C. and 1.2 mm Hg produced 31 g (0.24 mole) of diisopropyl-2,3 oxaziridine which was identified by infrared spectrography. The yield was 80%, compared to the imine used.

EXAMPLE 3

The operation was carried out as in Example 1, but hydrogen peroxide in the form of a 30% solution in water was used. The yield of cyclohexyl-2 isopropyl-3 oxaziridine collected after distillation was 89%, compared to the imine used.

EXAMPLE 4

The operation was carried out as in Example 1, but the isobutylidene cyclohexylamine was replaced by 29 g (0.4 mole) isobutyraldehyde and 39.6 g (0.4 mole) of cyclohexylamine. 60 g (0.355 mole) of cyclohexyl-2 isopropyl-3 oxaziridine were collected by distillation. The yield was 89%, compared to the isobutylraldehyde used.

EXAMPLE 5

The operation was carried out as in Example 2, but the isobutylidene isopropylamine was replaced by 54 g N-cyclohexylidene cyclohexylamine of 94.4% purity (0.285 mole). Distillation at 82° C. and 0.1–0.2 mm Hg produced 47 g (0.24 mole) of pentamethylene-N-cyclohexyloxaziridine which was identified by infrared spectrography. The yield was 84.5%, compared to the imine used.

EXAMPLE 6

DICYCLOHEXYL-2,2' BIOXAZIRIDINE-3,3'

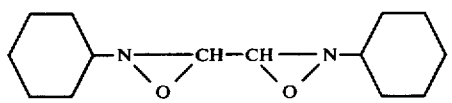

The operation was carried out as in Example 1, but isobutylidene cyclohexylamine was replaced by 44 g (0.2 mole) of N,N'glyoxylidene dicyclohexylamine. The reaction mixture was kept at 50° C. for 1 hour after the hydrogen peroxide was poured in, whereupon it was cooled and filtered. The resulting precipitate was washed with methanol and dried under reduced pressure. 38.3 g dicyclohexyl-2,2' bioxaziridine-3,3' of 88% purity (by chemical determination), which melts at 115° C. and was identified by infrared spectrography, was obtained.

EXAMPLE 7

A solution of 15 g (0.133 mole) isobutylidene isopropylamine, 0.4 g disodium salt of ethylenediaminetetracetic acid, and 0.27 g selenium in 17 g methanol was placed in a reactor, and then within a period of 1 hour, at 50° C., 8.2 g (0.166 mole) of a 69% aqueous solution of hydrogen peroxide were added. The reaction was allowed to continue for an additional 15 minutes, whereupon the selenium was filtered out; the methanol was eliminated under reduced pressure (200 mm Hg). Extraction was effected first with 25 cc of chloroform and then twice with 12 cc of chloroform. The organic phases were united and dried over sodium sulphate. The chloroform was evaporated under reduced pressure. Distillation of the residue at 43° C. and 1.2 mm Hg produced 12 g (0.003 mole) diisopropyl-2,3 oxaziridine, which was identified by infrared spectrography. The yield was 70%, compared to the imine used.

EXAMPLE 8

A solution of 0.6 g disodium salt of ethylenediametetracetic acid, 0.55 g selenium dioxide, and 10 g (0.2 mole) of a 68% aqueous solution of hydrogen peroxide in 25 g methanol was placed in a reactor. The pH of the solution was brought to 9.5 by the addition of 1 cc of 10 N soda, and then, while the temperature was maintained at 0° C., 29.4 g (0.4 mole) isobutylidene were added during a 15 minute period. The reaction was allowed to continue for an additional 45 minutes at 0° C., and then the methanol was eliminated at ambient temperature under reduced pressure (40 mm Hg). Extraction was effected first with 30 cc of cyclohexane and then twice with 15 cc of cyclohexane. The organic phases were united and then washed with a solution of sodium carbonate. The cyclohexane was evaporated at ambient temperature under reduced pressure (1 mm Hg). 30 g of a residue containing 0.1 mole phenyl-2 isopropyl-3 oxaziridine, which was identified by quantitative analysis and infrared spectrography, were recovered. The yield was 50%, compared to the hydrogen peroxide.

EXAMPLE 9

The operation was carried out as in Example 2, but the isobutylidene aniline was replaced by 34.6 (0.2 mole) cyclohexylidene aniline. After the methanol was evaporated under reduced pressure, the precipitate which formed was filtered and then washed twice with 20 cc of water. 43 g of a hydrated crystal was produced, which after recrystallization in the ether of mineral oil yielded 17.2 g phenyl-2 pentamethylene-3,3 oxaziridine, which melted at 77° C. and was identified by infrared spectrography.

EXAMPLE 10

A solution of 1 g calcium selenite dihydrate, 0.2 g disodium salt of ethylenediaminetetracetic acid, and 10 g (0.2 mole) of a 68% aqueous solution of hydrogen peroxide in 25 g methanol was placed in a reactor, and then within a period of 15 minutes, at 50° C., 22.6 g (0.2 mole) isobutylidene isopropylamine were added. The reaction was allowed to continue for an additional 45 minutes at 50° C., and then the calcium selenite was filtered out. The filtrate contained 21.9 g (0.170 mole) diisopropyl-2,3 oxaziridine. The yield was 85%, compared to the hydrogen peroxide used. The calcium selenite recovered by filtration was re-used in an identical process. The same yield of diisopropyl-2,3 oxaziridine was obtained.

EXAMPLE 11

The operation was carried out as in Example 10, but the isobutylidene isopropylamine was replaced by 30.6 g (0.2 mole) isobutylidene cyclohexylamine. The calcium selenite was filtered out, and then the methanol was removed under reduced pressure (100 mm Hg). Extraction was effected first with 25 cc of chloroform and then twice with 12 cc of chloroform. The organic phases were united and dried over sodium sulfate. The chloroform was evaporated under reduced pressure. Distillation of the residue at 43° C. and 0.2 mm Hg produced 28 g (0.166 mole) cyclohexyl-2 isopropyl-3 oxaziridine, which was identified by infrared spectography. The yield was 83%, compared to the hydrogen peroxide used. The calcium selenite recovered by filtration was re-used in an identical process. The same yield of cyclohexyl-2 isopropyl-3 oxaziridine was obtained.

We claim:
1. In the method of preparing oxaziridine which consists of reacting hydrogen peroxide with an azomethinic derivative or with a mixture of a carbonyl compound and a primary amine in the presence of a hydrogen peroxide catalyst, the improvement comprising carrying out the reaction in the presence of catalytic amounts of selenium or of oxygenated compounds of selenium.
2. A method according to claim 1, carried out in a solvent medium.
3. A method according to claim 2, in which the solvent used is a saturated alcohol containing 1 to 6 carbon atoms.

* * * * *